(12) United States Patent
Sasaki et al.

(10) Patent No.: US 10,619,184 B2
(45) Date of Patent: Apr. 14, 2020

(54) METHOD FOR DETECTING OCLN-ARHGAP26 GENE

(71) Applicants: Astellas Pharma Inc., Tokyo (JP); National Cancer Center, Tokyo (JP)

(72) Inventors: Hiroki Sasaki, Tokyo (JP); Hitoshi Ichikawa, Tokyo (JP); Makoto Asaumi, Tokyo (JP); Kazuhisa Tsunoyama, Tokyo (JP)

(73) Assignees: Astellas Pharma Inc., Tokyo (JP); National Cancer Center, Tokyo (JP)

( * ) Notice: Subject to any disclaimer, the term of this patent is extended or adjusted under 35 U.S.C. 154(b) by 25 days.

(21) Appl. No.: 15/753,775

(22) PCT Filed: Aug. 23, 2016

(86) PCT No.: PCT/JP2016/074440
§ 371 (c)(1),
(2) Date: Feb. 20, 2018

(87) PCT Pub. No.: WO2017/033905
PCT Pub. Date: Mar. 2, 2017

(65) Prior Publication Data
US 2018/0237862 A1    Aug. 23, 2018

Related U.S. Application Data

(60) Provisional application No. 62/209,095, filed on Aug. 24, 2015.

(30) Foreign Application Priority Data

Dec. 24, 2015    (JP) .................................. 2015-250996

(51) Int. Cl.
*C12Q 1/68* (2018.01)
*C12N 15/09* (2006.01)

(52) U.S. Cl.
CPC ............... *C12Q 1/68* (2013.01); *C12N 15/09* (2013.01); *C12Q 2600/112* (2013.01); *C12Q 2600/118* (2013.01); *C12Q 2600/156* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

2012/0258998 A1* 10/2012 Tan .................... A61K 31/7088
514/44 A

FOREIGN PATENT DOCUMENTS

| WO | WO2012/139134 A2 | 10/2012 |
| WO | WO2015/142293 A1 | 9/2015 |

OTHER PUBLICATIONS

New England Biolabs 1996/1997 catalog; p. 111 (Year: 1997).*
Wang et al. Nature Genetics, vol. 43, No. 12, pp. 1219-1223, including online methods (Year: 2011).*
Extended European Search Report for EP Application No. 16839252.0, dated Mar. 19, 2013.
International Search Report for PCT/JP2016/07440 dated Jan. 11, 2016.
Borkhardt, A et al, The human GRAF gene is fused to MLL in a unique t(5;11)(q31; q23) et al, Proc. Natl. Acad.Sci. USA, 2000, vol. 97, No. 16, pp. 9168-9173, Summary.
Osanai M. et al, Epigenetic silencing of occludin promotes tumorigenic and metastatic properties of cancer cells et al, Cancer Res., 2006, vol. 66, No. 18, pp. 9125-9133, sum.
Panagopoulos I et al, MLL/GRAF fusion in an infant (AML M5b) with a cytogenetically crytpic ins (5;11)(q31;q23q23), Genes Chromosomes Cancer,2004, vol. 41, No. 4, pp. 400-404,sum.
Yao F et al, Recurrent Fusion Genes in Gastric Cancer: CLDN18-ARHGAP26 Induces Loss of Epithelial Integrity, Cell Rep, Jul. 2015, vol. 12, No. 2, pp. 272-285, Summary.
Cancer Genome Atlas Research Network, Comprehensive molecular characterization of gastric adenocarcinoma, Nature, 2014, vol. 513, No. 7517, pp. 202-209, Fig 4.

* cited by examiner

*Primary Examiner* — Juliet C Switzer

(57) ABSTRACT

The object of the invention is to elucidate a new causative gene of cancer, polynucleotide, and thereby provide a method for detecting the polynucleotide or a polypeptide that is encoded by the polynucleotide, as well as a primer set or a detection kit for such detection. The detection method detects a fusion gene of a part of an OCLN gene and a part of an ARHGAP26 gene, or a fusion protein encoded by such gene. The primer set includes a sense primer designed from a section encoding OCLN and an antisense primer designed from a section encoding ARHGAP26.

5 Claims, 3 Drawing Sheets

Specification includes a Sequence Listing.

SEQUENCE LISTING

```
<160> NUMBER OF SEQ ID NOS: 10

<210> SEQ ID NO 1
<211> LENGTH: 2064
<212> TYPE: DNA
<213> ORGANISM: Homo sapiens
<220> FEATURE:
<221> NAME/KEY: CDS
<222> LOCATION: (1)..(2064)

<400> SEQUENCE: 1 atg tca tcc agg cct ctt gaa agt cca cct cct tac agg cct gat gaa      48
Met Ser Ser Arg Pro Leu Glu Ser Pro Pro Pro Tyr Arg Pro Asp Glu
1               5                   10                  15 ttc aaa ccg aat cat tat gca cca agc aat gac ata tat ggt gga gag      96
Phe Lys Pro Asn His Tyr Ala Pro Ser Asn Asp Ile Tyr Gly Gly Glu
            20                  25                  30 atg cat gtt cga cca atg ctc tct cag cca gcc tac tct ttt tac cca     144
Met His Val Arg Pro Met Leu Ser Gln Pro Ala Tyr Ser Phe Tyr Pro
        35                  40                  45 gaa gat gaa att ctt cac ttc tac aaa tgg acc tct cct cca gga gtg     192
Glu Asp Glu Ile Leu His Phe Tyr Lys Trp Thr Ser Pro Pro Gly Val
    50                  55                  60 att cgg atc ctg tct atg ctc att att gtg atg tgc att gcc atc ttt     240
Ile Arg Ile Leu Ser Met Leu Ile Ile Val Met Cys Ile Ala Ile Phe
65                  70                  75                  80 gcc tgt gtg gcc tcc acg ctt gcc tgg gac aga ggc tat gga act tcc     288
Ala Cys Val Ala Ser Thr Leu Ala Trp Asp Arg Gly Tyr Gly Thr Ser
                85                  90                  95 ctt tta gga ggt agt gta ggc tac cct tat gga gga agt ggc ttt ggt     336
Leu Leu Gly Gly Ser Val Gly Tyr Pro Tyr Gly Gly Ser Gly Phe Gly
            100                 105                 110 agc tac gga agt ggc tat ggc tat ggc tat ggt tat ggc tat ggc tac     384
Ser Tyr Gly Ser Gly Tyr Gly Tyr Gly Tyr Gly Tyr Gly Tyr Gly Tyr
        115                 120                 125 gga ggc tat aca gac cca aga gca gca aag ggc ttc atg ttg gcc atg     432
Gly Gly Tyr Thr Asp Pro Arg Ala Ala Lys Gly Phe Met Leu Ala Met
    130                 135                 140 gct gcc ttt tgt ttc att gcc gcg ttg gtg atc ttt gtt acc agt gtt     480
Ala Ala Phe Cys Phe Ile Ala Ala Leu Val Ile Phe Val Thr Ser Val
145                 150                 155                 160 ata aga tct gaa atg tcc aga aca aga aga tac tac tta agt gtg ata     528
Ile Arg Ser Glu Met Ser Arg Thr Arg Arg Tyr Tyr Leu Ser Val Ile
                165                 170                 175 ata gtg agt gct atc ctg ggc atc atg gtg ttt att gcc aca att gtc     576
Ile Val Ser Ala Ile Leu Gly Ile Met Val Phe Ile Ala Thr Ile Val
            180                 185                 190 tat ata atg gga gtg aac cca act gct cag tct tct gga tct cta tat     624
Tyr Ile Met Gly Val Asn Pro Thr Ala Gln Ser Ser Gly Ser Leu Tyr
        195                 200                 205 ggt tca caa ata tat gcc ctc tgc aac caa ttt tat aca cct gca gct     672
Gly Ser Gln Ile Tyr Ala Leu Cys Asn Gln Phe Tyr Thr Pro Ala Ala
    210                 215                 220 act gga ctc tac gtg gat cag tat ttg tat cac tac tgt gtt gtg gat     720
Thr Gly Leu Tyr Val Asp Gln Tyr Leu Tyr His Tyr Cys Val Val Asp
225                 230                 235                 240
```

```
ccc cag gag gcc att gcc att gta ctg ggg ttc atg att att gtg gct        768
Pro Gln Glu Ala Ile Ala Ile Val Leu Gly Phe Met Ile Ile Val Ala
            245                 250                 255 ttt gct tta ata att ttc ttt gct gtg aaa act cga aga aag atg gac        816
Phe Ala Leu Ile Ile Phe Phe Ala Val Lys Thr Arg Arg Lys Met Asp
            260                 265                 270 agg tat gac aag tcc aat att ttg tgg gac aag gaa cac att tat gat        864
Arg Tyr Asp Lys Ser Asn Ile Leu Trp Asp Lys Glu His Ile Tyr Asp
                275                 280                 285 gag cag ccc ccc aat gtc gag gag tgg gtc tac aac tcg aac aaa gac        912
Glu Gln Pro Pro Asn Val Glu Glu Trp Val Tyr Asn Ser Asn Lys Asp
            290                 295                 300 agc cag agt gaa ggg act gcg cag ttg gac agc att ggc ttc agc ata        960
Ser Gln Ser Glu Gly Thr Ala Gln Leu Asp Ser Ile Gly Phe Ser Ile
305                 310                 315                 320 atc agg aaa tgc atc cat gct gtg gaa acc aga ggg atc aac gag caa       1008
Ile Arg Lys Cys Ile His Ala Val Glu Thr Arg Gly Ile Asn Glu Gln
                325                 330                 335 ggg ctg tat cga att gtg ggg gtc aac tcc aga gtg cag aag ttg ctg       1056
Gly Leu Tyr Arg Ile Val Gly Val Asn Ser Arg Val Gln Lys Leu Leu
            340                 345                 350 agt gtc ctg atg gac ccc aag act gct tct gag aca gaa aca gat atc       1104
Ser Val Leu Met Asp Pro Lys Thr Ala Ser Glu Thr Glu Thr Asp Ile
            355                 360                 365 tgt gct gaa tgg gag ata aag acc atc act agt gct ctg aag acc tac       1152
Cys Ala Glu Trp Glu Ile Lys Thr Ile Thr Ser Ala Leu Lys Thr Tyr
370                 375                 380 cta aga atg ctt cca gga cca ctc atg atg tac cag ttt caa aga agt       1200
Leu Arg Met Leu Pro Gly Pro Leu Met Met Tyr Gln Phe Gln Arg Ser
385                 390                 395                 400 ttc atc aaa gca gca aaa ctg gag aac cag gag tct cgg gtc tct gaa       1248
Phe Ile Lys Ala Ala Lys Leu Glu Asn Gln Glu Ser Arg Val Ser Glu
                405                 410                 415 atc cac agc ctt gtt cat cgg ctc cca gag aaa aat cgg cag atg tta       1296
Ile His Ser Leu Val His Arg Leu Pro Glu Lys Asn Arg Gln Met Leu
            420                 425                 430 cag ctg ctc atg aac cac ttg gca aat gtt gct aac aac cac aag cag       1344
Gln Leu Leu Met Asn His Leu Ala Asn Val Ala Asn Asn His Lys Gln
            435                 440                 445 aat ttg atg acg gtg gca aac ctt ggt gtg gtg ttt gga ccc act ctg       1392
Asn Leu Met Thr Val Ala Asn Leu Gly Val Val Phe Gly Pro Thr Leu
            450                 455                 460 ctg agg cct cag gaa gaa aca gta gca gcc atc atg gac atc aaa ttt       1440
Leu Arg Pro Gln Glu Glu Thr Val Ala Ala Ile Met Asp Ile Lys Phe
465                 470                 475                 480 cag aac att gtc att gag atc cta ata gaa aac cac gaa aag ata ttt       1488
Gln Asn Ile Val Ile Glu Ile Leu Ile Glu Asn His Glu Lys Ile Phe
                485                 490                 495 aac acc gtg ccc gat atg cct ctc acc aat gcc cag ctg cac ctg tct       1536
Asn Thr Val Pro Asp Met Pro Leu Thr Asn Ala Gln Leu His Leu Ser
            500                 505                 510 cgg aag aag agc agt gac tcc aag ccc ccg tcc tgc agc gag agg ccc       1584
Arg Lys Lys Ser Ser Asp Ser Lys Pro Pro Ser Cys Ser Glu Arg Pro
            515                 520                 525 ctg acg ctc ttc cac acc gtt cag tca aca gag aaa cag gaa caa agg       1632
Leu Thr Leu Phe His Thr Val Gln Ser Thr Glu Lys Gln Glu Gln Arg
            530                 535                 540 aac agc atc atc aac tcc agt ttg gaa tct gtc tca tca aat cca aac       1680
Asn Ser Ile Ile Asn Ser Ser Leu Glu Ser Val Ser Ser Asn Pro Asn
545                 550                 555                 560
```

-continued

```
agc atc ctt aat tcc agc agc agc tta cag ccc aac atg aac tcc agt    1728
Ser Ile Leu Asn Ser Ser Ser Ser Leu Gln Pro Asn Met Asn Ser Ser
            565                 570                 575 gac cca gac ctg gct gtg gtc aaa ccc acc cgg ccc aac tca ctc ccc    1776
Asp Pro Asp Leu Ala Val Val Lys Pro Thr Arg Pro Asn Ser Leu Pro
        580                 585                 590 ccg aat cca agc cca act tca ccc ctc tcg cca tct tgg ccc atg ttc    1824
Pro Asn Pro Ser Pro Thr Ser Pro Leu Ser Pro Ser Trp Pro Met Phe
            595                 600                 605 tcg gcg cca tcc agc cct atg ccc acc tca tcc acg tcc agc gac tca    1872
Ser Ala Pro Ser Ser Pro Met Pro Thr Ser Ser Thr Ser Ser Asp Ser
        610                 615                 620 tcc ccc gtc agc aca ccg ttc cgg aag gca aaa gcc ttg tat gcc tgc    1920
Ser Pro Val Ser Thr Pro Phe Arg Lys Ala Lys Ala Leu Tyr Ala Cys
625                 630                 635                 640 aaa gct gaa cat gac tca gaa ctt tcg ttc aca gca ggc acg gtc ttc    1968
Lys Ala Glu His Asp Ser Glu Leu Ser Phe Thr Ala Gly Thr Val Phe
                645                 650                 655 gat aat gtt cac cca tct cag gag cct ggc tgg ttg gag ggg act ctg    2016
Asp Asn Val His Pro Ser Gln Glu Pro Gly Trp Leu Glu Gly Thr Leu
            660                 665                 670 aac gga aag act ggc ctc atc cct gag aat tac gtg gag ttc ctc taa    2064
Asn Gly Lys Thr Gly Leu Ile Pro Glu Asn Tyr Val Glu Phe Leu
        675                 680                 685
```

<210> SEQ ID NO 2
<211> LENGTH: 687
<212> TYPE: PRT
<213> ORGANISM: Homo sapiens

<400> SEQUENCE: 2

```
Met Ser Ser Arg Pro Leu Glu Ser Pro Pro Tyr Arg Pro Asp Glu
1               5                   10                  15

Phe Lys Pro Asn His Tyr Ala Pro Ser Asn Asp Ile Tyr Gly Gly Glu
                20                  25                  30

Met His Val Arg Pro Met Leu Ser Gln Pro Ala Tyr Ser Phe Tyr Pro
            35                  40                  45

Glu Asp Glu Ile Leu His Phe Tyr Lys Trp Thr Ser Pro Pro Gly Val
    50                  55                  60

Ile Arg Ile Leu Ser Met Leu Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Gly Ser Gly Phe Gly
            100                 105                 110

Ser Tyr Gly Ser Gly Tyr Gly Tyr Gly Tyr Gly Tyr Gly Tyr Gly Tyr
        115                 120                 125

Gly Gly Tyr Thr Asp Pro Arg Ala Ala Lys Gly Phe Met Leu Ala Met
    130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
            180                 185                 190

Tyr Ile Met Gly Val Asn Pro Thr Ala Gln Ser Ser Gly Ser Leu Tyr
        195                 200                 205
```

```
Gly Ser Gln Ile Tyr Ala Leu Cys Asn Gln Phe Tyr Thr Pro Ala Ala
    210                 215                 220

Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
            260                 265                 270

Arg Tyr Asp Lys Ser Asn Ile Leu Trp Asp Lys Glu His Ile Tyr Asp
        275                 280                 285

Glu Gln Pro Pro Asn Val Glu Glu Trp Val Tyr Asn Ser Asn Lys Asp
    290                 295                 300

Ser Gln Ser Glu Gly Thr Ala Gln Leu Asp Ser Ile Gly Phe Ser Ile
305                 310                 315                 320

Ile Arg Lys Cys Ile His Ala Val Glu Thr Arg Gly Ile Asn Glu Gln
                325                 330                 335

Gly Leu Tyr Arg Ile Val Gly Val Asn Ser Arg Val Gln Lys Leu Leu
            340                 345                 350

Ser Val Leu Met Asp Pro Lys Thr Ala Ser Glu Thr Glu Thr Asp Ile
        355                 360                 365

Cys Ala Glu Trp Glu Ile Lys Thr Ile Thr Ser Ala Leu Lys Thr Tyr
    370                 375                 380

Leu Arg Met Leu Pro Gly Pro Leu Met Met Tyr Gln Phe Gln Arg Ser
385                 390                 395                 400

Phe Ile Lys Ala Ala Lys Leu Glu Asn Gln Glu Ser Arg Val Ser Glu
                405                 410                 415

Ile His Ser Leu Val His Arg Leu Pro Glu Lys Asn Arg Gln Met Leu
            420                 425                 430

Gln Leu Leu Met Asn His Leu Ala Asn Val Ala Asn His Lys Gln
        435                 440                 445

Asn Leu Met Thr Val Ala Asn Leu Gly Val Val Phe Gly Pro Thr Leu
    450                 455                 460

Leu Arg Pro Gln Glu Glu Thr Val Ala Ala Ile Met Asp Ile Lys Phe
465                 470                 475                 480

Gln Asn Ile Val Ile Glu Ile Leu Ile Glu Asn His Glu Lys Ile Phe
                485                 490                 495

Asn Thr Val Pro Asp Met Pro Leu Thr Asn Ala Gln Leu His Leu Ser
            500                 505                 510

Arg Lys Lys Ser Ser Asp Ser Lys Pro Pro Ser Cys Ser Glu Arg Pro
        515                 520                 525

Leu Thr Leu Phe His Thr Val Gln Ser Thr Gly Lys Gln Glu Gln Arg
    530                 535                 540

Asn Ser Ile Ile Asn Ser Ser Leu Glu Ser Val Ser Ser Asn Pro Asn
545                 550                 555                 560

Ser Ile Leu Asn Ser Ser Ser Leu Gln Pro Asn Met Asn Ser Ser
                565                 570                 575

Asp Pro Asp Leu Ala Val Val Lys Pro Thr Arg Pro Asn Ser Leu Pro
            580                 585                 590

Pro Asn Pro Ser Pro Thr Ser Pro Leu Ser Pro Ser Trp Pro Met Phe
        595                 600                 605

Ser Ala Pro Ser Ser Pro Met Pro Thr Ser Ser Thr Ser Ser Asp Ser
    610                 615                 620
```

```
Ser Pro Val Ser Thr Pro Phe Arg Lys Ala Lys Ala Leu Tyr Ala Cys
625                 630                 635                 640

Lys Ala Glu His Asp Ser Glu Leu Ser Phe Thr Ala Gly Thr Val Phe
            645                 650                 655

Asp Asn Val His Pro Ser Gln Glu Pro Gly Trp Leu Glu Gly Thr Leu
        660                 665                 670

Asn Gly Lys Thr Gly Leu Ile Pro Glu Asn Tyr Val Glu Phe Leu
    675                 680                 685

<210> SEQ ID NO 3
<211> LENGTH: 18
<212> TYPE: DNA
<213> ORGANISM: Homo sapiens

<400> SEQUENCE: 3
cgagcggatt ggtttatc                                                    18

<210> SEQ ID NO 4
<211> LENGTH: 18
<212> TYPE: DNA
<213> ORGANISM: Homo sapiens

<400> SEQUENCE: 4
acgctgcatt tctcagtg                                                    18

<210> SEQ ID NO 5
<211> LENGTH: 18
<212> TYPE: DNA
<213> ORGANISM: Homo sapiens

<400> SEQUENCE: 5
agctaaaggg cattgctc                                                    18

<210> SEQ ID NO 6
<211> LENGTH: 18
<212> TYPE: DNA
<213> ORGANISM: Homo sapiens

<400> SEQUENCE: 6
ctggaatcag cagttgtc                                                    18

<210> SEQ ID NO 7
<211> LENGTH: 18
<212> TYPE: DNA
<213> ORGANISM: Homo sapiens

<400> SEQUENCE: 7
atacacctgc agctactg                                                    18

<210> SEQ ID NO 8
<211> LENGTH: 18
<212> TYPE: DNA
<213> ORGANISM: Homo sapiens

<400> SEQUENCE: 8
cctggaagca ttcttagg                                                    18

<210> SEQ ID NO 9
<211> LENGTH: 20
<212> TYPE: DNA
<213> ORGANISM: Homo sapiens

<400> SEQUENCE: 9
```

```
gaagtccctt gccatcctaa                                               20

<210> SEQ ID NO 10
<211> LENGTH: 20
<212> TYPE: DNA
<213> ORGANISM: Homo sapiens

<400> SEQUENCE: 10
gcacgaaggc tcatcattca                                               20
```

METHOD FOR DETECTING OCLN-ARHGAP26 GENE

This application is a national stage filing under 35 U.S.C. § 371 of PCT/JP2016/074440, filed Aug. 23, 2016, which claims priority to U.S. Provisional Patent Application No. 62/209,095 filed Aug. 24, 2015, and Japanese Patent Application No. 250996/2015, filed Dec. 24, 2015, the contents of which are each incorporated herein by reference in their entireties.

This application incorporates-by-reference the sequence listing contained in the text file named OS10200_Sequence Listing.txt, which was created on Feb. 8, 2018 and is 19.8 kb in size.

TECHNICAL FIELD

The present invention relates to a method for detecting a novel fusion gene.

BACKGROUND ART

Occludin (OCLN) gene exists on the long arm of human chromosome 5, and a protein encoded by this gene is a four transmembrane protein. OCLN forms a complex with a claudin family protein that is also a four transmembrane protein and constitutes a tight junction (J Cell Biol. 1998; 143(2): 391-401) and enhances electric resistance between cells by over-expression of OCLN in cells (J Cell Sci. 1996; 109: 2287-2298). As such, OCLN is considered to hold a role in the barrier function of tight junction. With regards to cancer, over-expression of OCLN in cells is reported to enhance the apoptosis signal and to suppress metastatic potential (Cancer Res. 2006; 66(18): 9125-9133).

Rho GTPase activating protein 26 (ARHGAP26) gene, which has GTPase activating function exists on the long arm of human chromosome 5, same as OCLN, and the protein encoded by this gene is a GTPase activating protein possessing a Rho-GAP domain at the center. ARHGAP26 gene is known to have a function to enhance the GTP hydrolase activity of the small GTPase protein family, particularly RhoA and CDC42 (J Biol Chem. 2000; 275(49): 38605-38610). With regards to cancer, a fusion gene with claudin 18 (CLDN18) gene was found in 3 to 15% of patients suffered from diffuse type gastric cancer (Nature 2014; 513(7517): 202-209, Cell Rep. 2015; 12(2): 272-285), and a fusion gene with a mixed-lineage leukemia (MLL) gene was found in leukemia patients (Proc Natl Acad Sci USA. 2000; 97(16): 9168-9173, Genes Chromosomes Cancer 2004; 41(4): 400-404).

There are no reports so far of a fusion gene composed of OCLN and ARHGAP26.

SUMMARY OF INVENTION

Problem to be Solved by Invention

The present invention aims to elucidate a polynucleotide as a novel gene responsible for cancer, and thereby to provide a method for detecting a polynucleotide or a polypeptide that is encoded by the polynucleotide, as well as a primer set or a detection kit for such detection.

Means for Solving the Problems

The present inventors isolated and identified a novel fusion gene from a stomach cancer cell line, in which a part of the ARHGAP26 gene and a part of the OCLN gene are fused together (Example 1), and found that this fusion gene was the causal cancer gene by the fact that the viability of the stomach cancer cell line declined with the suppression of expression of fusion genes in the stomach cancer cell line that endogenously expresses such fusion genes (Example 2, Example 4). The present inventors constructed a detection method of a fusion gene based on these findings, and provided primer sets for such purpose, thereby using the detection of such fusion gene made it possible to select cancer patients (particularly, stomach cancer patients) that test positive for a fusion gene composed of an OCLN gene and an ARHGAP26 gene (Example 3).

In other words, the present invention relates to [1] to [24] shown below.

[1] A method for detecting a fusion gene composed of an occludin (OCLN) gene and a Rho GTPase activating protein 26 (ARHGAP26) gene, wherein the method comprises a step of detecting whether a polynucleotide that encodes a polypeptide described by either (1) or (2) shown below exists in a sample obtained from a subject:

(1) a polypeptide that comprises an amino acid sequence having no less than 90% identity with an amino acid sequence represented by SEQ ID NO: 2;

(2) a polypeptide that comprises an amino acid sequence represented by SEQ ID NO: 2, or a polypeptide that comprises an amino acid sequence represented by SEQ ID NO: 2, in which 1 to 10 amino acids are deleted, substituted, inserted and/or added.

[2] The method according to [1], wherein the polypeptide comprises an amino acid sequence having no less than 90% identity with an amino acid sequence represented by SEQ ID NO: 2, and has an ability to develop tumor.

[3] The method according to [1], wherein the polypeptide comprises an amino acid sequence represented by SEQ ID NO: 2 and has an ability to develop tumor, or the polypeptide comprises an amino acid sequence represented by SEQ ID NO: 2, in which 1 to 10 amino acids are deleted, substituted, inserted and/or added, and has an ability to develop tumor.

[4] The method according to [1], wherein the polypeptide consists of an amino acid sequence represented by SEQ ID NO: 2.

[5] A method for detecting a fusion gene composed of an OCLN gene and an ARHGAP26 gene comprising a step of detecting whether a polynucleotide that encodes a polypeptide consisting of an amino acid sequence represented by SEQ ID NO: 2 exists in a sample obtained from a subject.

[6] The method according to any one of [1] to [5] further comprising a step in which it is judged when a polynucleotide targeted in detection is detected, that a fusion gene composed of an OCLN gene, and an ARHGAP26 gene exists.

[7] The method according to any one of [1] to [6], further comprising a step of amplifying a nucleic acid existing in a sample obtained from a subject, or a step of hybridizing a probe with a nucleic acid existing in a sample obtained from a subject to detect a polynucleotide targeted in detection.

[8] The method according to [7] comprising a step of amplifying the nucleic acid existing in a sample obtained from a subject using a primer set shown below:

a primer set for detecting a fusion gene composed of an OCLN gene and an ARHGAP26 gene, the primer set comprising a sense primer designed from a section encoding OCLN and an antisense primer designed from a section encoding ARHGAP26, wherein the antisense primer consists of an oligonucleotide that hybridizes under a stringent condition with a polynucleotide targeted in detection, and the sense primer consists of an oligonucleotide that hybridizes under a stringent condition with a complementary strand of a polynucleotide targeted in detection.

[9] The method according to [8], wherein the sense primer consists of an oligonucleotide that hybridizes under a stringent condition with a complementary strand of a polynucleotide consisting of base no. 1 to 891 of SEQ ID NO: 1, and the antisense primer consists of an oligonucleotide that hybridizes under a stringent condition with a polynucleotide consisting of base no. 892 to 2064 of SEQ ID NO: 1.

[10] The method according to any one of [7] to [9] comprising a step of amplifying the nucleic acid existing in a sample obtained from a subject using a primer set shown below:

a primer set for detecting a fusion gene composed of an OCLN gene and an ARHGAP26 gene, wherein a sense primer consists of an oligonucleotide of at least 16 random consecutive bases between base no. 1 to 891 of SEQ ID NO: 1, and an antisense primer consists of an oligonucleotide complementary to an oligonucleotide of at least 16 random consecutive bases between base no. 892 to 2064 of SEQ ID NO: 1.

[11] The method according to any one of [7] to [10] further comprising a step of detecting whether an amplified nucleic acid fragment of a target size was obtained.

[12] The method according to [11] further comprising a step in which it is judged when an amplified nucleic acid fragment of a target size is obtained, that a fusion gene composed of an OCLN gene and an ARHGAP26 gene exists.

[13] The method according to any one of [7] to [10] further comprising a step of determining a base sequence of an amplified nucleic acid fragment.

[14] The method according to [13] further comprising a step in which it is judged when an amplified nucleic acid fragment includes a base sequence of a section encoding OCLN and a base sequence of a section encoding ARHGAP26 in a same fragment, that a fusion gene composed of an OCLN gene and an ARHGAP26 gene exists.

[15] The method according to [7] comprising a step of hybridizing a probe with the nucleic acid existing in a sample obtained from a subject, wherein the probe comprises an oligonucleotide that hybridizes with the polynucleotide under a stringent condition.

[16] The method according to [15] comprising a step of performing in situ hybridization using a sample obtained from a subject, a probe designed from a section encoding OCLN of the polynucleotide, and a probe designed from a section encoding ARHGAP26 of the polynucleotide.

[17] The method according to [16] using multiple types of probes designed from a section encoding OCLN, and multiple types of probes designed from a section encoding ARHGAP26.

[18] The method according to [7], [16] or [17] using multiple types of adjacent probe pairs comprising an oligonucleotide that is complementary to an oligonucleotide of at least 16 random consecutive bases between base no. 1 to 891 of SEQ ID NO: 1, and multiple types of adjacent probe pairs comprising an oligonucleotide that is complementary to an oligonucleotide of at least 16 random consecutive bases between base no. 892 to 2064 of SEQ ID NO: 1, in a step of hybridizing a probe with the nucleic acid existing in a sample obtained from a subject.

[19] The method according to any one of [16] to [18] further comprising a step of amplifying hybridization signals.

[20] The method according to any one of [16] to [19] further comprising a step of detecting a signal overlap of a signal from a probe designed from a section encoding OCLN and a signal from a probe designed from a section encoding ARHGAP26.

[21] The method according to [20] further comprising a step in which it is judged when two signals are detected at a same position, that a fusion gene composed of an OCLN gene and an ARHGAP26 gene exists.

[22] The method according to any one of [1] to [21] comprising a step of obtaining a sample from a subject.

[23] The method according to any one of [1] to [22], wherein the subject is a cancer patient.

[24] The method according to [23], wherein cancer is stomach cancer.

Further, the present invention relates to [25] to [27] shown below.

[25] A method for detecting whether cancer exists in a subject comprising the step according to any one of [1] to [21].

[26] The method according to [25] comprising a step of obtaining a sample from a subject.

[27] The method according to [25] or [26], wherein cancer is stomach cancer.

Further, the present invention relates to [28] to [32] shown below.

[28] The method for diagnosing cancer in a subject comprising a step according to any one of [1] to [21].

[29] The method according to [28] comprising a step of obtaining a sample from a subject.

[30] The method according to [28] or [29] further comprising a step in which it is judged when a fusion gene composed of an OCLN gene and an ARHGAP26 gene is detected in a sample obtained from a subject, that there is a high possibility of the subject having cancer.

[31] The method according to [28] or [29], wherein cancer is stomach cancer.

[32] The method according to [29] further comprising a step in which it is judged when a fusion gene composed of an OCLN gene and an ARHGAP26 gene is detected in a sample obtained from a subject, that there is a high possibility of a subject having stomach cancer.

Further, the present invention relates to [33] to [36] shown below.

[33] A method for identifying a subject that is a candidate for receiving a treatment by an ARHGAP26 function inhibitor and/or a pharmaceutical agent for blocking an abnormal signal induced by a fusion gene composed of an OCLN gene and an ARHGAP26 gene, comprising a step according to any one of [1] to [21], wherein the subject is a cancer patient.

[34] The method according to [33] comprising a step of obtaining a sample from a subject.

[35] The method according to [33] or [34] further comprising a step in which it is judged when a fusion gene composed of an OCLN gene and an ARHGAP26 gene is detected in a sample obtained from a subject, that the subject is a candidate for receiving a treatment by an ARHGAP26 inhibitor and/or a pharmaceutical agent for blocking an abnormal signal induced by a fusion gene composed of an OCLN gene and an ARHGAP26 gene.

[36] The method according to any one of [33] or [35], wherein cancer is stomach cancer.

Further, the present invention relates to [37] to [42] shown below.

[37] A primer set for detecting a fusion gene composed of an OCLN gene and an ARHGAP26 gene existing in a sample obtained from a subject, the primer set comprising a sense primer designed from a section encoding OCLN and an antisense primer designed from a section encoding ARHGAP26, wherein the antisense primer consists of an oligonucleotide that hybridizes under a stringent condition with the polynucleotide according to any one of [1] to [5], and the sense primer consists of an oligonucleotide that hybridizes under a stringent condition with a complementary strand of the polynucleotide.

[38] The primer set according to [37], wherein the sense primer consists of an oligonucleotide that hybridizes under a stringent condition with a complementary strand of a polynucleotide consisting of base no. 1 to 891 of SEQ ID NO: 1, and the antisense primer consists of an oligonucleotide that hybridizes under a stringent condition with a polynucleotide consisting of base no. 892 to 2064 of SEQ ID NO: 1.

[39] A primer set for detecting a fusion gene composed of an OCLN gene and an ARHGAP26 gene existing in a sample obtained from a subject, the primer set comprising a sense primer designed from a section encoding OCLN or an antisense primer designed from a section encoding ARHGAP26 of the polynucleotide according to any one of [1] to [5].

[40] The primer set according to any one of [37] to [39], wherein the sense primer consists of an oligonucleotide of at least 16 random consecutive bases between base no. 1 to 891 of SEQ ID NO: 1, and the antisense primer consists of an oligonucleotide that is complementary to an oligonucleotide of at least 16 random consecutive bases between base no. 892 to 2064 of SEQ ID NO: 1.

[41] The primer set according to any one of [37] to [40], wherein the subject is a cancer patient.

[42] The primer set according to [41], wherein cancer is stomach cancer.

Further, the present invention relates to [43] to [48] shown below.

[43] A probe for detecting a fusion gene composed of an OCLN gene and an ARHGAP26 gene existing in a sample obtained from a subject, the probe comprising an oligonucleotide that hybridizes under a stringent condition with the polynucleotide according to any one of [1] to [5].

[44] The probe set comprising multiple probes according to [43], the probe set comprising a probe designed from a section encoding OCLN and a probe designed from a section encoding ARHGAP26 of the polynucleotide according to any one of [1] to [5].

[45] The probe set according to [44] comprising multiple types of probes designed from a section encoding OCLN and multiple types of probes designed from a section encoding ARHGAP26.

[46] The probe set according to [44] or [45] comprising multiple types of adjacent probe pairs comprising an oligonucleotide that is complementary to an oligonucleotide of at least 16 random consecutive bases between base no. 1 to 891 of SEQ ID NO: 1 and multiple types of adjacent probe pairs comprising an oligonucleotide that is complementary to an oligonucleotide of at least 16 random consecutive bases between base no. 892 to 2064 of SEQ ID NO: 1.

[47] The probe or a probe set according to any one of [43] to [46], wherein the subject is a cancer patient.

[48] The probe or the probe set according to [47], wherein cancer is stomach cancer.

Further, the present invention relates to [49] to [53] shown below.

[49] A detection kit for detecting a fusion gene composed of an OCLN gene and an ARHGAP26 gene existing in a sample obtained from the subject, the detection set comprising a primer set according to any one of [37] to [40].

[50] A detection kit for detecting a fusion gene composed of an OCLN gene and an ARHGAP26 gene existing in a sample obtained from a subject, the detection kit comprising a probe or a probe set according to any one of [43] to [46].

[51] The detection kit according to [50] further comprising a reagent for amplifying a signal of hybridization.

[52] The detection kit according to any one of [49] to [51], wherein the subject is a cancer patient.

[53] The detection kit according to [52], wherein cancer is stomach cancer.

Further, the present invention relates to [54] to [63] shown below.

[54] A detection method of a fusion protein of OCLN and ARHGAP26 comprising a step of detecting whether a polypeptide according to either (1) or (2) exists in a sample obtained from a subject:
(1) a polypeptide that comprises an amino acid sequence having no less than 90% identity with an amino acid sequence represented by SEQ ID NO: 2;
(2) a polypeptide that comprises an amino acid sequence represented by SEQ ID NO: 2, or a polypeptide that comprises an amino acid sequence represented by SEQ ID NO: 2, in which 1 to 10 amino acids are deleted, substituted, inserted and/or added.

[55] The method according to [54], wherein the polypeptide comprises an amino acid sequence having no less than 90% identity with an amino acid sequence represented by SEQ ID NO: 2, and has an ability to develop tumor.

[56] The method according to [54], wherein the polypeptide comprises an amino acid sequence represented by SEQ ID NO: 2 and has an ability to develop tumor, or the polypeptide comprises an amino acid sequence represented by SEQ ID NO: 2, in which 1 to 10 amino acids are deleted, substituted, inserted and/or added, and has an ability to develop tumor.

[57] The method according to [54], wherein the polypeptide consists of an amino acid sequence represented by SEQ ID NO: 2.

[58] A detection method of a fusion protein of OCLN and ARHGAP26 comprising a step of detecting whether a polypeptide consisting of an amino acid sequence represented by SEQ ID NO: 2 exists in a sample obtained from a subject.

[59] The method according to any one of [54] to [58], wherein the step for detecting whether the polypeptide exists comprises a step of bringing an antibody (primary antibody) that recognizes a section derived from an OCLN gene in the polypeptide and an antibody (primary antibody) that recognizes a section derived from an ARHGAP26 gene in the polypeptide in contact with a sample obtained from a subject.

[60] The method according to [59] further comprising steps of i) to v) described below:
i) a step of adding secondary antibodies that are connected to oligonucleotides and that respectively bind to primary antibodies; ii) a step of adding a ligation solution that contains two types of oligonucleotides that are partially complementary to oligonucleotides connected to the secondary antibodies and a ligase that can ligate the two types of oligonucleotides to form a circular structure when the oligonucleotides approach each other, thereby inducing a ligation reaction; iii) a step of elongating a nucleic acid along a circular structure that is formed; and iv) a step of hybridizing a labeled oligonucleotide probe that can hybridize with an elongated nucleic acid, and v) a step of detecting a labeled signal.

[61] The method according to any one of [54] to [60] comprising a step of obtaining a sample from a subject.

[62] The method according to any one of [54] to [61], wherein the subject is a cancer patient.

[63] The method according to [62], wherein cancer is stomach cancer.

Further, the present invention relates to [64] to [66] shown below.

[64] A method for detecting whether cancer exists in a subject comprising the step according to any one of [54] to [60].

[65] The method according to [64] comprising a step of obtaining a sample from a subject.

[66] The method according to [64] or [65], wherein cancer is stomach cancer.

Further, the present invention relates to [67] to [71] shown below.

[67] A method for diagnosing cancer in a subject comprising a step according to any one of [54] to [60].

[68] The method according to [67] comprising a step of obtaining a sample from a subject.

[69] The method according to [67] or [68] further comprising a step in which it is judged when a fusion protein of OCLN and ARHGAP26 is detected in a sample obtained from a subject, that there is a high possibility of the subject having cancer.

[70] The method according to [67] or [68], wherein cancer is stomach cancer.

[71] The method according to [68] further comprising a step in which it is judged when a fusion protein of OCLN and ARHGAP26 is detected in a sample obtained from a subject, that there is a high possibility of the subject having stomach cancer.

Further, the present invention relates to [72] to [75] shown below.

[72] A method for identifying a subject that is a candidate for receiving a treatment by an ARHGAP26 function inhibitor and/or a pharmaceutical agent for blocking an abnormal signal induced by a fusion gene composed of an OCLN gene and an ARHGAP26 gene, the method comprising a step according to any one of [54] to [60], wherein the subject is a cancer patient.

[73] The method according to [72] comprising a step of obtaining a sample from a subject.

[74] The method according to [72] or [73] further comprising a step in which it is judged when a fusion protein of OCLN and ARHGAP26 is detected in a sample obtained from a subject, that the subject is a candidate for receiving a treatment by an ARHGAP26 inhibitor and/or a pharmaceutical agent for blocking an abnormal signal induced by a fusion gene composed of an OCLN gene and an ARHGAP26 gene.

[75] The method according to [72] or [74], wherein cancer is stomach cancer.

Further, the present invention relates to [76] to [79] shown below.

[76] A detection kit for detecting a fusion protein of OCLN and ARHGAP26 existing in a sample obtained from a subject, the detection kit comprising an antibody (primary antibody) that recognizes a section derived from an OCLN gene in the polypeptide according to any one of [54] to [58], and an antibody (primary antibody) that recognizes a section derived from an ARHGAP26 gene in said polypeptide.

[77] The detection kit according to [76] comprising secondary antibodies that are connected to oligonucleotides and that respectively bind to primary antibodies, two types of oligonucleotides that are partially complementary to the oligonucleotides connected to the secondary antibodies, a ligase that can ligate the two types of oligonucleotides to form a circular structure when the oligonucleotides approach each other, and a labeled oligonucleotide probe.

[78] The detection kit according to [76] or [77], wherein the subject is a cancer patient.

[79] The detection kit according to [78], wherein cancer is stomach cancer.

Further, the present invention relates to [80] to [81] shown below.

[80] A polypeptide according to any one of (1) to (3) shown below or a polynucleotide encoding said polypeptide:

(1) a polypeptide that comprises an amino acid sequence having no less than 90% identity with an amino acid sequence represented by SEQ ID NO: 2;

(2) a polypeptide that comprises an amino acid sequence represented by SEQ ID NO: 2, in which 1 to 10 amino acids are deleted, substituted, inserted and/or added; (3) a polypeptide consisting of an amino acid sequence represented by SEQ ID NO: 2.

[81] The polypeptide or a polynucleotide encoding said polypeptide according to [80] that has an ability to develop tumor.

Advantageous Effect of Invention

The detection method of the present invention may be used as a method for detecting cancer (particularly, stomach cancer) that tests positive for a fusion gene composed of an OCLN gene and an ARHGAP26 gene (hereinafter referred to as OCLN-ARHGAP26 fusion gene). The primer set, probe, probe set and detection kit of the present invention may be used in a detection method of the present invention.

BRIEF DESCRIPTION OF DRAWINGS

FIG. 2 compares the number of viable cells cultured in a 0.5% bovine serum containing RPMI-1640 medium after introduction of siRNA with that of the control.

DESCRIPTION OF EMBODIMENTS

Figure 1:
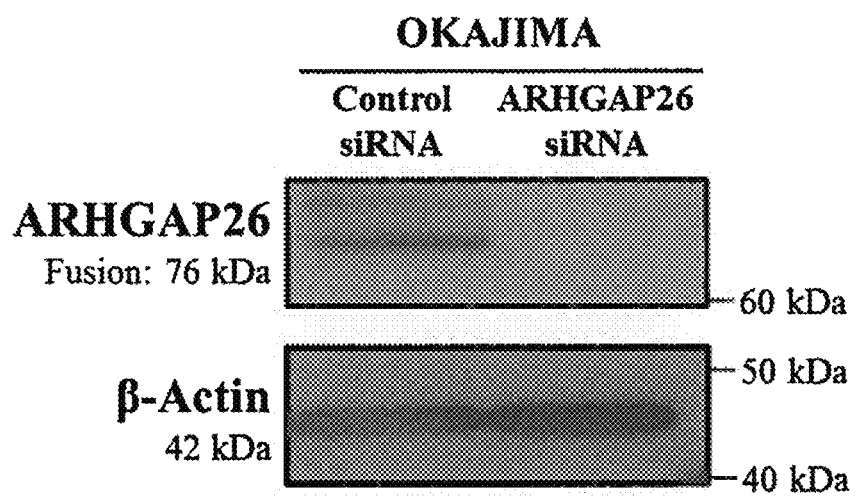
FIG. 1 shows the result of the Western blot. It shows the change in the amount of protein expression of the OCLN-ARHGAP26 fusion protein by the ARHGAP26 siRNA treatment.

《 Detection Method of the Present Invention 》

The detection method of the present invention includes a method for detecting a fusion gene, and a method for detecting a fusion protein encoded in the fusion gene. The method for detecting a fusion gene of the present invention or the method for detecting a fusion protein of the present invention includes a step of detecting whether a specific polynucleotide or polypeptide exists in a sample obtained from a subject.

Items collected from the subject (samples separated from a living body) are used as the sample obtained from the subject, specifically, any cells, tissues, or body fluids that were collected (blood, oral mucus, circulating tumor cells, exosome, etc.), biopsied samples (samples from the primary focus, cancer cells in the peritoneal lavage solution, cancer cells in ascites, etc.), of which the biopsied samples are preferred. It is possible to use genome DNAs extracted from the collected samples or to use transcription products thereof (products that are obtained by transcription and translation of a genome; e.g. RNA, protein) or cDNA prepared from RNA. Using RNA or cDNA that had been formulated is preferred. It is also possible to use a stabilized sample fixed in formalin and embedded in paraffin (Formalin—Fixed Paraffin—Embedded sample; FFPE Sample). A FFPE sample sliced into a thin FFPE slice may also be used. A use of a FFPE slice enables a direct detection of a polynucleotide existing in the slice.

The method for detecting a fusion gene in the present invention is a method for detecting "a fusion gene composed of an OCLN gene and an ARHGAP26 gene," wherein the fusion gene is a fusion gene comprising a part of an OCLN gene and a part of an ARHGAP26 gene. An exemplary fusion gene composed of an OCLN gene and an ARHGAP26 gene includes a polynucleotide consisting of a base sequence represented by SEQ ID NO: 1. The polynucleotide consisting of a base sequence represented by SEQ ID NO: 1 is a polynucleotide with a base sequence of base no. 207 (corresponding to the 5' terminal of the coding sequence (hereinafter referred to as CDS)) to 1097 of an OCLN gene (GenBank registration no: NM_001205254.1) and base no. 1143 to 2315 (corresponding to the 3' terminal of CDS) of an ARHGAP26 gene (GenBank registration no: NM_001135608.1), in which thymine at base no. 1280 is substituted with guanine, and cytosine at base no. 2225 is substituted with thymine. Of the base sequence represented by SEQ ID NO: 1, the sequence from base no. 1 to 891 is derived from an OCLN gene, and the sequence from base no. 892 to 2064 is derived from an ARHGAP26 gene. The polynucleotide consisting of a base sequence represented by SEQ ID NO: 1 is also referred to as a "fusion polynucleotide." The amino acid sequence encoded in base no. 1 to 2064 of SEQ ID NO: 1 is shown in SEQ ID NO: 2.

In the "step of detecting whether a polynucleotide exists" in the detection method of a fusion gene of the present invention, the polynucleotide that is the target of detection (referred to in the present specification as the "polynucleotide targeted in detection") includes, for example, a polynucleotide encoding a polypeptide described in (1) or (2) shown below:

(1) a polypeptide that comprises an amino acid sequence having no less than 90% identity with an amino acid sequence represented by SEQ ID NO: 2;
(2) a polypeptide that comprises an amino acid sequence having no less than 90% identity with an amino acid sequence represented by SEQ ID NO: 2, and has an ability to develop tumor.

In the aforementioned polypeptide, the "identity with an amino acid sequence represented by SEQ ID NO: 2" is preferably 95% or higher, and more preferably 98% or higher.

Note that the "identity" as used in the present specification is a value of "Identity" obtained by using a parameter prepared by default by the NEEDLE program (J Mol Biol 1970; 48: 443-453) search. The aforementioned parameter is shown below.
Gap penalty=10
Extend penalty=0.5
Matrix=EBLOSUM62

Whether a polypeptide "has an ability to develop tumor" or not may be confirmed by a method shown below in Example 2. One specific method is to introduce siRNA that suppresses the expression of a polynucleotide encoding the polypeptide to a cell expressing the polypeptide (stomach cancer cell line OKAJIMA), and to verify that the viability of the cell decreases.

In one embodiment of the present invention, the polynucleotide targeted in detection is a polynucleotide encoding a polypeptide according to any one of (1) to (4) shown below:

(1) a polypeptide that comprises an amino acid sequence represented by SEQ ID NO: 2, in which 1 to 10 amino acids are deleted, substituted, inserted and/or added;
(2) a polypeptide that comprises an amino acid sequence represented by SEQ ID NO: 2, in which 1 to 10 amino acids are deleted, substituted, inserted and/or added, and has an ability to develop tumor;
(3) a polypeptide that comprises an amino acid sequence represented by SEQ ID NO: 2 and has an ability to develop tumor; and
(4) a polypeptide that consists of an amino acid sequence represented by SEQ ID NO: 2.

In the polypeptide of (1) and (2), the number of amino acids that had been deleted, substituted, inserted and/or added in the amino acid sequence represented by SEQ ID NO: 2 is preferably one to a few, more preferably 1 to 7, and even more preferably 1 to 5.

An example of a polynucleotide that encodes "a polypeptide that consists of an amino acid sequence represented by SEQ ID NO: 2" includes "a polynucleotide that consists of a base sequence represented by SEQ ID NO: 1."

The method for detecting a fusion gene of the present invention may comprise a step in which it is judged whether the polynucleotide targeted in detection exists by whether the polynucleotide was detected.

The method for detecting a fusion gene of the present invention may further comprise a step in which it is judged when a polynucleotide targeted in detection is detected, that a fusion gene composed of an OCLN gene and an ARHGAP26 gene exists.

The method for detecting a fusion gene of the present invention may comprise a step of amplifying the nucleic acid existing in the sample obtained from a subject or a step of hybridizing a probe with the nucleic acid existing in the sample obtained from a subject to detect the polynucleotide targeted in detection.

The nucleic acid for use may be a genome DNA, RNA or a cDNA prepared from RNA. The methods of extracting DNA, extracting RNA or preparing cDNA from RNA is commonly known in the field, and it may be performed easily by using a commercially available DNA extraction kit, RNA extraction kit or a cDNA synthesis kit.

The step of amplifying a nucleic acid in the sample obtained from a subject may be performed by a commonly known method of amplifying a nucleic acid. Such method includes PCR (Polymerase chain reaction, e.g. real-time PCR), LCR (Ligase chain reaction), SDA (Strand displacement amplification), NASBA (Nucleic acid sequence-based amplification), ICAN (Isothermal and chimeric primer-initiated amplification of nucleic acids), LAMP (Loop-mediated isothermal amplification), TMA (Transcription-mediated amplification, e.g. Gen-Probe's TMA system), and a preferable method is PCR.

Specifically, the nucleic acid (e.g. genome DNA, RNA, or cDNA prepared from RNA, etc.) in the sample obtained from a subject is subjected to a nucleic acid amplification reaction using a primer set designed to specifically amplify a polynucleotide targeted in detection. The primer set to be used is not particularly limited as long as it can specifically amplify a polynucleotide targeted in detection. For example, a use of a primer design software (e.g. Primer Express; Applied Biosystems) allows a person skilled in the art to easily design the primer set based on the base sequence of a polynucleotide targeted in detection. More specifically, a primer set includes a sense primer (5'-primer) designed from a section that encodes the OCLN of a polynucleotide targeted in detection (e.g. any section in an OCLN gene region of the fusion polynucleotide (particularly, cDNA)) and an antisense primer (3'-primer) designed from a section encoding ARHGAP26 of a polynucleotide targeted in detection (e.g. any section in an ARHGAP26 gene region of the fusion polynucleotide (particularly, cDNA)), and the antisense primer consists of an oligonucleotide that hybridizes with a polynucleotide targeted in detection under a stringent condition (preferably, under a highly stringent condition), and the sense primer consists of an oligonucleotide that hybridizes with a complementary strand of a polynucleotide targeted in detection under a stringent condition (preferably, under a highly stringent condition). Otherwise, either the sense primer or the antisense primer may be designed so that it corresponds to the region comprising the fusion point of the polynucleotide targeted in detection.

The "stringent condition" in the present specification refers to a hybridization condition of "5×SSPE, 5×Denhardt's solution, 0.5% SDS, 50% formaldehyde, 200 µg/mL salmon sperm DNA, at 42° C. overnight" and a washing condition of "0.5×SSC, 0.1% SDS, 42° C." "A highly stringent condition" refers to a hybridization condition of "5×SSPE, 5×Denhardt's solution, 0.5% SDS, 50% formaldehyde, 200 µg/mL salmon sperm DNA, at 42° C. overnight" and a washing condition of "0.2×SSC, 0.1% SDS, 65° C."

The "fusion point" of the polynucleotide targeted in detection in the present specification is a point in which a section derived from an OCLN gene and a section derived from an ARHGAP26 gene in the polynucleotide targeted in detection are fused together, and the "region comprising the fusion point" in the polynucleotide targeted in detection is, for example, the region comprising bases of base no. 891 and 892 when the polynucleotide targeted in detection is a polynucleotide consisting of a base sequence represented by SEQ ID NO: 1.

In an embodiment of the present invention, the sense primer consists of an oligonucleotide hybridizing with a complementary strand of a polynucleotide that consists of base no. 1 to 891 of SEQ ID NO: 1 under a stringent condition, and the antisense primer consists of an oligonucleotide hybridizing with a polynucleotide that consists of base no. 892 to 2064 of SEQ ID NO: 1 under a stringent condition.

In an embodiment of the present invention, the sense primer consists of at least 16 consecutive bases of an oligonucleotide between base no. 1 to 891 of SEQ ID NO: 1, and the antisense primer consists of an oligonucleotide that is complementary with at least 16 consecutive bases of an oligonucleotide that consists of base no. 892 to 2064 of SEQ ID NO: 1.

In a step to amplify nucleic acid, the sense primer and the antisense primer should preferably be set so that the fragment size of the nucleic acid to be amplified is 1 kb or lower, since a large fragment size of the nucleic acid to be amplified leads to poor amplification efficiency. The primers to be used generally have a chain length of at least 15 bases, preferably at least 16 bases, more preferably at least 18 bases, even more preferably at least 20 bases. In one embodiment of the present invention, the primer has 15 to 40 bases, preferably 16 to 24 bases, more preferably 18 to 24 bases, even more preferably 20 to 24 bases.

The primer may be produced by chemical synthesis without being particularly limited thereby.

In a preferable embodiment, the detection method of a fusion gene of the present invention further encompasses a step of detecting whether an amplified nucleic acid fragment of a desired size was obtained in addition to a step of amplifying nucleic acid in the sample obtained from a subject. The step of detecting whether an amplified nucleic acid fragment of a desired size was obtained may be performed using electrophoresis. By using electrophoresis, the nucleic acid fragment may be analyzed by agarose gel electrophoresis to confirm whether amplified nucleic acid fragments were produced in the desired size by using ethidium bromide dye, etc.

Further, by performing a PCR amplification monitor in the amplification process of the gene (real time PCR) (Genome Res. 1996; 6(10): 986-994), it is possible to perform a quantified analysis of amplified nucleic acid fragments. A possible candidate to be used in the PCR amplification monitoring method is ABI PRISM7900 (Applied Biosystems).

When an amplified nucleic acid fragment of the desired size is obtained, that means that a polynucleotide targeted in detection existed in the sample obtained from a subject. The detection method of a fusion gene of the present invention may further include a step in which it is judged when an amplified nucleic acid fragment of the desired size is obtained, that a fusion gene composed of an OCLN gene and an ARHGAP26 gene exists.

In a separate preferable embodiment, the detection method of the fusion gene of the present invention further encompasses a step of determining the base sequence of the amplified nucleic acid in addition to a step of amplifying the nucleic acid of the sample obtained from a subject. The step of determining the base sequence of the nucleic acid fragment may use sequencing methods commonly known in the field of art including next generation sequencing methods (Nature Biotechnology 2008; 26: 1135-1145) (e.g. HiSeq2500 (Illumina)), such as the Sanger sequencing (e.g. ABI PRISM3100 (Applied Biosystems) may be used), or sequencing by synthesis, etc.

The step of determining the base sequence of the nucleic acid fragment includes not just a step of sequencing the full length of a nucleic acid fragment, but a step of sequencing partial sequences corresponding to both ends of the nucleic acid fragment.

When the sequenced nucleic acid fragment includes a base sequence of a section encoding OCLN and a base sequence of a section encoding ARHGAP26 of the polynucleotide targeted in detection in the same fragment, that means that the polynucleotide targeted in detection existed in the sample obtained from a subject. The detection method of the fusion gene of the present invention may further include a step in which it is judged when the amplified nucleic acid fragment includes a base sequence of a section encoding OCLN and a base sequence of a section encoding ARHGAP26 of the polynucleotide targeted in detection in the same fragment, that a fusion gene composed of an OCLN gene and an ARHGAP26 gene exists.

The step of hybridizing a probe with a nucleic acid in the sample obtained from a subject may be performed using a probe including oligonucleotide that hybridizes under a stringent condition (preferably, under a highly stringent condition) with a polynucleotide targeted in detection, and using a commonly known hybridization method. Such methods include, for example, Northern hybridization, dot blot method, DNA micro array method, RNA protection method, in situ hybridization, etc. A preferable method is the in situ hybridization. Detection using the in situ hybridization may be performed by a commonly known fluorescent in situ hybridization (FISH), chromogenic in situ hybridization (CISH), or silver in situ hybridization (SISH). The chain length of the probe used in hybridization may be selected as necessary by a person skilled in the art according to the hybridization method to be used, but the probe preferably has a chain length of at least 16 bases.

In one embodiment of the present invention, the probe used in hybridization is an oligonucleotide that hybridizes under a stringent condition (preferably, under a highly stringent condition) with a polynucleotide targeted in detection, or a complementary strand thereof, and it includes an oligonucleotide of at least 16 bases upstream and at least 16 bases downstream of the fusion point on the polynucleotide targeted in detection (a specific example being a sequence of base no. 876 to 907 in SEQ ID NO: 1) or an oligonucleotide that is complementary to said oligonucleotide.

In one embodiment of the present invention, the step of hybridizing a probe with a nucleic acid existing in a sample obtained from a subject may be performed according to the commonly known RNA FISH method (J. Mol. Diagn. 2012; 14(1): 22-29). More specifically, in situ hybridization is performed using a sample obtained from a subject (e.g. FFPE fragment), a probe designed from a section encoding OCLN of the polynucleotide targeted in detection (e.g. any section in an OCLN gene region of the fusion polynucleotide), and a probe designed from a section encoding ARHGAP26 of the polynucleotide targeted in detection (e.g. any section in an ARHGAP26 gene region of the fusion polynucleotide). The probes include oligonucleotides that hybridize under a stringent condition (preferably, under a highly stringent condition) with the polynucleotide targeted in detection.

In one embodiment of the present invention, the in situ hybridization is performed using multiple detection probes designed from a section encoding OCLN and multiple detection probes designed from a section encoding ARHGAP26.

In one embodiment of the present invention, the in situ hybridization is performed using the following probes:

multiple types of adjacent probe pairs including oligonucleotides that are complementary to at least 16 random consecutive oligonucleotides in base no. 1 to 891 of SEQ ID NO: 1 (preferably 10 to 25 types, more preferably 18 to 22 types, even more preferably 20 types of probe pairs), and multiple types of adjacent probe pairs including oligonucleotides that are complementary to at least 16 random consecutive oligonucleotides in base no. 892 to 2064 of SEQ ID NO: 1 (preferably 10 to 25 types, more preferably 18 to 22 types, even more preferably 20 types of probe pairs).

The "adjacent probe pairs" in the present specification consist of two types of probes that are arranged next to each other when they hybridize with the polynucleotide targeted in detection. The probes include an oligonucleotide that is complementary to the polynucleotide targeted in detection, and the length of the oligonucleotide is generally at least 16 bases, preferably at least 18 bases. In one embodiment of the present invention, the length of the oligonucleotide is 16 to 30 bases, preferably 18 to 25 bases.

In a preferable embodiment of the present invention, the detection method of the fusion gene of the present invention further encompasses a step of amplifying a hybridization signal in addition to a step of performing in situ hybridization. To perform a step of amplifying a hybridization signal, a reagent that amplifies a hybridization signal may be hybridized with a probe that hybridizes with a nucleic acid contained in the sample.

Reagents that amplify a hybridization signal used in in situ hybridization include PreAmplifier Mix QT, Amplifier Mix QT, Label Probe Mix, and Label Probe Diluent QF, which may be obtained from Affymetrix.

In a more preferable embodiment, the detection method of the fusion gene of the present invention further encompasses a step of detecting a signal overlap between a signal from a probe designed from a section encoding OCLN and a signal from a probe designed from a section encoding ARHGAP26. By separating the fluorescent reagent or the color reagent that detects a probe designed from a section encoding OCLN and a probe designed from a section encoding ARHGAP26, it is possible to observe whether the signals from the two different probes are in the same area (inside the same molecule). When it is observed that the signals from the two different probes are in the same area (inside the same molecule), that would mean that the polynucleotide targeted in detection existed in the sample obtained from a subject. The detection method of the fusion gene of the present invention may further include a step in which it is judged when the two signals are in the same area (inside the same molecule), that a fusion gene composed of an OCLN gene and an ARHGAP26 gene exists.

The probes are not particularly limited, but they may be produced by a chemical synthesis method.

The detection method of the fusion protein of the present invention is a method for detecting "a fusion protein of OCLN and ARHGAP26" and the fusion protein is a fusion protein encoded by the fusion gene of the OCLN gene and the ARHGAP26 gene.

In the "step of detecting whether polypeptide exists" in the detection method of the fusion protein of the present invention, the polypeptide targeted in detection includes a polypeptide that is encoded by a polynucleotide targeted in detection.

The detection method of the fusion protein of the present invention may encompass a step in which it is judged whether a polynucleotide exists by whether the polypeptide targeted in detection is detected.

The detection method of the fusion protein of the present invention may further encompass a step in which it is judged when the polypeptide targeted in detection is detected, that a fusion protein of OCLN and ARHGAP26 exists.

The step of detecting whether a polypeptide exists may be performed by preparing a lysate derived from a sample obtained from a subject (e.g. cancer tissue or cell obtained from a subject) and measuring the polypeptide targeted in detection, contained in the sample by an immunological measurement method or an enzyme active measurement method, which combine antibodies against proteins that constitute the fusion protein, or a detection method that combines these methods, or by mass spectrometry. Further, this step may be performed by a detection method using an immunological tissue staining technology performed by combining the polypeptide targeted in detection included in the sample (e.g. FFPE fragment) obtained from a subject, that had appropriately undergone pretreatment (such as, removal of paraffin), with the antibodies against proteins constituting the fusion protein. Otherwise, this step may be performed by exchanging the antibodies against proteins constituting the fusion protein to antibodies that recognize the fusion section of the fusion protein. Exemplary approaches to these methods include the following methods using monoclonal antibodies and polyclonal antibodies specific to the polypeptide targeted in detection: enzyme immunizing measurement, double antibody sandwich ELISA method, fluorescent immunological measurement method, radioimmunological measurement method, Western blot, immunohistologic staining, a detection method combining immune precipitation and mass spectrometry, etc.

The "fusion section" of the fusion protein of the present specification refers to a section in the polypeptide targeted in detection, in which the section derived from an OCLN gene and a section derived from an ARHGAP26 gene are fused.

The detection using an immunohistologic staining technology may be performed according to Proximity Ligation Assay (Nat. Methods. 2006; 3(12): 995-1000). More specifically, whether the polypeptide targeted in detection exists or not may be detected by using an antibody that recognizes a section derived from the OCLN gene of the polypeptide targeted in detection, and an antibody that recognizes a section derived from an ARHGAP26 gene of a polypeptide targeted in detection, and by detecting that the two antibodies recognize the same molecule by the aforementioned technologies. More specifically, the detection may be performed by i) a step of bringing an antibody (primary antibody) that recognizes a section derived from an OCLN gene of polypeptide targeted in detection, and the antibody (primary antibody) that recognizes a section derived from an ARHGAP26 gene of polypeptide targeted in detection, in contact with the sample obtained from the subject; ii) a step of adding secondary antibodies that are connected to oligonucleotides, and binds to the respective primary antibodies, iii) a step of inducing ligation by adding two types of oligonucleotides that are partly complementary to oligonucleotides connected to the secondary antibodies, and a ligation solution containing ligase that can form a circular structure by ligation of the two types of oligonucleotides when they approach each other; iv) a step of elongating a nucleic acid along the circular structure that was formed, v) a step of hybridizing a labeled oligonucleotide probe that can hybridize with the elongated nucleic acid; and vi) a step of detecting the labeling signal. Such detection may be performed using a PLA probe and reagents included in the Duolink II reagent kit or the Duolink II Bright field reagent kit (Olink).

In one embodiment of the present invention, the detection method of the present invention encompasses a step of obtaining a sample from the subject.

In one embodiment of the present invention, the subject of the detection method of the present invention is a cancer patient, and in a more specific embodiment, the cancer is stomach cancer. The type of stomach cancer is not particularly limited, but it may be a diffuse type, an intestinal type, or a mix type in the Lauren classification. Further, without being limited thereby, the stomach cancer may be any of papillary adenocarcinoma, tubular adenocarcinoma, poorly differentiated adenocarcinoma, signet ring cell carcinoma, or carcinoma mucoid, etc.

In the detection method of the present invention, it is possible to judge when the polynucleotide targeted in detection, or the polypeptide targeted in detection is detected in the sample obtained from the subject, that the subject has cancer (particularly, stomach cancer).

The detection step in the detection method of the present invention may be used as a method for detecting whether cancer (particularly, stomach cancer) exists in a subject or a method for diagnosing cancer (particularly, stomach cancer) in the subject. The diagnosis method of the present invention may include, in addition to the aforementioned detection step, a step in which it is judged when the polynucleotide targeted in detection, or the polypeptide targeted in detection is detected in the sample obtained from the subject, that there is a high possibility that the subject has cancer (particularly, stomach cancer). Further, the detection step may be used in a method for identifying a subject (a cancer patient of stomach cancer, etc.) that is a candidate for receiving a treatment by an ARHGAP26 function inhibitor and/or a pharmaceutical agent that blocks abnormality signal induced by a fusion gene composed of an OCLN gene and an ARHGAP26 gene. The identification method of the present invention may include, in addition to the detection step, a step in which it is judged when a polynucleotide is detected in a sample obtained from the subject, that the subject is a candidate for receiving a treatment by an ARHGAP26 function inhibitor and/or a pharmaceutical agent that blocks abnormality signal induced by a fusion gene composed of an OCLN gene and an ARHGAP26 gene.

《 The Primer Set, Probe, Probe Set and Detection Kit of the Present Invention 》

The present invention encompasses a primer set, probe, probe set and a detection kit used in the detection method of the present invention.

The primer set of the present invention includes a sense primer designed from a section encoding OCLN and an antisense primer designed from a section encoding ARHGAP26, and the antisense primer consists of an oligonucleotide that hybridizes with the polynucleotide targeted in detection under a stringent condition (preferably, under a highly stringent condition), and the sense primer consists of an oligonucleotide that hybridizes with a complementary strand of a polynucleotide targeted in detection under a stringent condition (preferably, under a highly stringent condition).

In the primer set of the present invention, either the sense primer or the antisense primer may be designed so that it corresponds to a region in a polynucleotide targeted in detection that comprises a fusion point.

A specific embodiment of the primer set of the present invention includes the following primer set:

a primer set consisting of a sense primer consisting of an oligonucleotide that hybridizes under a stringent condition with a complementary strand of a polynucleotide consisting of base no. 1 to 891 of SEQ ID NO: 1 and an antisense primer consisting of an oligonucleotide that hybridizes under a stringent condition with a polynucleotide consisting of base no. 892 to 2064 of SEQ ID NO: 1.

A more specific embodiment of the primer set of the present invention includes the following primer set:

a primer set consisting of a sense primer consisting of an oligonucleotide of at least 16 random consecutive bases between base no. 1 to 891 of SEQ ID NO: 1 and an antisense primer consisting of an oligonucleotide that is complementary with at least 16 random consecutive bases between base no. 892 to 2064 of SEQ ID NO: 1.

It is preferable for the primer set to have a space of 1 kb or lower between the selected positions of the sense primer and the antisense primer, or a nucleic acid fragment amplified by the sense primer and the antisense primer with a size of 1 kb or lower. Further, the primer of the present invention normally has a chain length of at least 15 bases, preferably at least 16 bases, more preferably at least 18 bases, even more preferably at least 20 bases. In one embodiment of the present invention, the primer has a chain length of 15 to 40 bases, preferably 16 to 24 bases, more preferably 18 to 24 bases, and even more preferably 20 to 24 bases.

The primers included in the primer set of the present invention, without being particularly limited, may be produced by a chemical synthesis method.

The probes included in the probe of the present invention and the probe set of the present invention includes an oligonucleotide that hybridizes with the polynucleotide targeted in detection under a stringent condition (preferably, under a highly stringent condition). The chain length of the probes included in the probe of the present invention or the probe set of the present invention may be selected as necessary by a person skilled in the art according to the applied hybridization method, but the probe preferably has a chain length of at least 16 bases.

In one embodiment of the present invention, the probe of the present invention includes an oligonucleotide of at least 16 bases upstream and at least 16 bases downstream of the fusion point in the polynucleotide targeted in detection (specifically, the sequence between base no. 876 to 907 of SEQ ID NO: 1), or an oligonucleotide that is complementary thereto.

In one embodiment of the present invention, the probe set of the present invention includes a probe designed from a section encoding OCLN (e.g. any section in the OCLN gene region of the fusion polynucleotide) and a probe designed from a section encoding ARHGAP26 (e.g. any section in the ARHGAP26 gene region of the fusion polynucleotide).

In one embodiment of the present invention, the probe set of the present invention includes multiple types of probes designed from a section encoding OCLN and multiple types of probes designed from a section encoding ARHGAP26.

In one embodiment of the present invention, the probe set of the present invention includes the following:

multiple types of adjacent probe pairs including an oligonucleotide that is complementary to an oligonucleotide of at least 16 random consecutive bases between base no. 1 to 891 of SEQ ID NO: 1 (preferably 10 to 25 types, more preferably 18 to 22 types, even more preferably 20 types of probe pairs), and multiple types of adjacent probe pairs including an oligonucleotide that is complementary with an oligonucleotide of at least 16 random consecutive bases between base no. 892 to 2064 of SEQ ID NO: 1 (preferably 10 to 25 types, more preferably 18 to 22 types, even more preferably 20 types of probe pairs).

The probes of the probe pair include an oligonucleotide that is complementary with the polynucleotide targeted in detection, and the length of the oligonucleotide is normally at least 16 bases, preferably at least 18 bases. In one embodiment of the present invention, the length of the oligonucleotide is 16 to 30 bases, preferably 18 to 25 bases.

The probe of the present invention and the probe included in the probe set of the present invention, without being limited thereby, may be produced by chemical synthesis.

The present invention encompasses a detection kit including a primer set of the present invention, a probe of the present invention or the probe set of the present invention. The detection kit of the present invention may include in addition to the primer set of the present invention, the probe of the present invention or the probe set of the present invention, components that may be used together with the primer set, the probe or the probe set for the detection of a polynucleotide targeted in detection such as reagents to amplify the signal of hybridization.

The present invention also encompasses a detection kit for detecting a polypeptide targeted in detection. Preferably, the detection kit includes an antibody (primary antibody) that recognizes a section derived from an OCLN gene of polypeptide targeted in detection, and an antibody (primary antibody) that recognizes a section derived from an ARHGAP26 gene of polypeptide targeted in detection. More preferably, the present invention may include secondary antibodies connected with oligonucleotides that are respectively bound to primary antibodies, two types of oligonucleotides that are partially complementary to the oligonucleotides connected to the secondary antibodies, ligase that forms a circular structure by ligation of the two types of oligonucleotides when they approach each other, and labeled oligonucleotide probes.

The primer set, probe, probe set, and detection kit of the present invention may be used for the detection method, diagnosis method, identification method of a patient, and identification method of a subject of the present invention. In one embodiment of the present invention, with respect to the primer set, probe, probe set and detection kit of the present invention, the subject is a cancer patient and more specifically, the cancer is stomach cancer. The stomach cancer is not particularly limited, but it may be a diffuse type, an intestinal type, or a mix type in the Lauren classification. Further, without being limited thereby, the stomach cancer may be any of papillary adenocarcinoma, tubular adenocarcinoma, poorly differentiated adenocarcinoma, signet ring cell carcinoma, or carcinoma mucoid.

EXAMPLES

The Examples may be performed by commonly known methods unless otherwise indicated. When using commercially available reagents or kits, the Examples may be performed according to the manuals of the commercial products.

Example 1 Isolation of OCLN-ARHGAP26 Fusion Gene

Total RNA was prepared from OKAJIMA, a stomach cancer cell line provided from First Department of Pathology, Hiroshima University School of Medicine (currently, Department of Molecular Pathology, Graduate School of Biomedical and Health Sciences, Hiroshima University), and reverse-transcribed into cDNA with a reverse transcriptase (SuperScriptIII; Life Technologies) and Oligo(dT) Primer (Oligo(dT)20 Primer; Life Technologies) according to the standard protocol of the reagent.

Next, primers of OCLN_full fwd21 represented by SEQ ID NO: 3 and ARHGAP26_full rev01 represented by SEQ ID NO: 4 were used to perform PCR (10 sec. at 98° C., 15 sec. at 55° C., and 3 min. at 68° C., 30 cycles, followed by 5 min. at 68° C.) using DNA polymerase (PrimeSTAR GXL; TAKARA BIO INC.) with cDNA obtained in above step as a template. Then, using the aforementioned PCR product diluted by 10-fold as a template, primers of OCLN_full fwd22 represented by SEQ ID NO: 5 and ARHGAP26_full rev02 represented by SEQ ID NO: 6 were used to perform PCR (10 sec. at 98° C., 15 sec. at 55° C., and 3 min. at 68° C., 30 cycles, followed by 5 min. at 68° C.) using the same DNA polymerase. Electrophoresis was performed after the PCR to obtain a PCR product of about 2 kbp. After adding A to the 3'-end of the PCR product using Takara Taq (TAKARA BIO INC.), it was cloned into a cloning vector (TOPO XL PCR Cloning Kit; Life Technologies) and sequenced by dideoxy sequencing method (BigDye Terminator v3.1 Cycle Sequencing Kit; Life Technologies). Consequently, the PCR product that is about 2 kbp derived from the stomach cancer cell line OKAJIMA was found to be a transcription product (SEQ ID NO: 1) in which a nucleotide sequence of base no. 207 (corresponding to the 5' terminal of CDS) to 1097 of OCLN (NM_001205254.1) registered in NCBI is fused to a nucleotide sequence of base no. 1143 to 2315 of ARHGAP26 (NM_001135608.1) (corresponding to the 3' terminal of CDS) with substitutions of thymine to guanine at base no. 1280 and cytosine to thymine at base no. 2225. The amino acid sequence of a polypeptide encoded in SEQ ID NO: 1 is represented by SEQ ID NO: 2.

Example 2 Evaluation of Ability to Suppress Expression of OCLN-ARHGAP26 Fusion Protein in a Stomach Cancer Cell Line Expressing OCLN-ARHGAP26 Fusion Gene Using ARHGAP26 siRNA, and Evaluation of Viability of the Cell Line Under the Condition After culturing the stomach cancer cell line OKAJIMA that expresses OCLN-ARHGAP26 fusion gene, as shown in Example 1 in RPMI-1640 medium (Wako Pure Chemical Industries, Ltd.) containing 10% bovine serum (Gibco), siRNA was introduced into the cells according to the standard protocol of the transfection reagent DharmaFECT1 (GE Healthcare). Specifically, the above cancer cells were seeded at $2 \times 10^5$ cells per well to a 6 well plate (140675, Nunc). 75 pmol of siRNA that targets ARHGAP26 (s23013, Life Technologies) and control siRNA (AM4611, Life Technologies) were added to the cells (final concentration 75 nM), and the cells were cultured at 37° C. under an environment of 5% $CO_2$ for 120 h. (hereinafter, the group in which control siRNA was transfected is referred to as the Control siRNA group, and the group in which siRNA that targets ARHGAP26 is transfected is referred to as the ARHGAP26 siRNA group).

The suppressive effect of OCLN-ARHGAP26 fusion protein by siRNA treatment was evaluated by the Western blot analysis. Specifically, the cultured cells were dissolved in 350 mM dithiothreitol (Fermentas)-containing Laemmli Sample Buffer (Bio-Rad) to extract protein. Protein concentration was measured by Protein Quantification Assay (MA-CHEREY-NAGEL GmbH & Co. KG). The protein extract was loaded onto a 8% or 12% Poly-Acrylamide gel (Serva) containing SDS (Wako Pure Chemical Industries, Ltd.) so that 5 µg or 20 µg of protein was loaded onto each lane and gel electrophoresis was performed for 1 h. under a condition of 40 mA. After 80 min. of transfer to a PVDF membrane (Millipore Corporation) under a 60 mA condition using TRANS-BLOT SD SEMI-DRY TRANSFER CELL (Bio-Rad), blocking was performed for 2 h. at room temperature using PBS containing 5% Membrane Blocking Agent (GE Healthcare) (hereinafter referred to as the blocking buffer). The membrane was shaken in a primary antibody solution of anti-ARHGAP26 antibody (HPA035107, Sigma-Aldrich) diluted with a blocking buffer to a rate of 1:500 and anti-β-Actin antibody (4967, Cell Signaling Technology) diluted with a blocking buffer to a rate of 1:3000, and incubated overnight at 4° C. After washing with PBS containing 0.05% Tween 20 (Wako Pure Chemical Industries, Ltd.) (hereinafter referred to as the washing buffer), the membrane was shaken in a secondary antibody solution of HRP labeled anti-rabbit antibody (P0399, Daco) diluted with a blocking buffer to a rate of 1:3000, and incubated for 1 h. at room temperature. After washing with a washing buffer, Pierce Western blot Substrate Plus (Thermo Fisher Scientific Inc.) was added onto the membrane, and the chemiluminescence on a membrane was detected using LAS-4000R (Fuji Film). As a result of Western blotting, it was confirmed that the expression of OCLN-ARHGAP26 fusion protein was suppressed by the siRNA that targets ARHGAP26 (FIG. 1).

Next, in order to evaluate the effect of the OCLN-ARHGAP26 fusion gene on the viability of the cancer cells, siRNA that targets ARHGAP26 and the control siRNA were introduced into the stomach cancer cell line OKAJIMA under the same conditions as shown above. After 24 h., the medium was changed to a RPMI-1640 medium containing 0.5% bovine serum, and the cells were seeded at $1 \times 10^3$ cells per well to a 96 well plate (167008, Nunc), at 100 µL each, so that cells of each group were seeded to 6 wells, and cultured for additional 48 h. at 37° C. under a 5% $CO_2$ environment. wells containing only RPMI-1640 medium containing 10% bovine serum without cells was prepared as a control (hereinafter referred to as the medium group). The number of living cells was measured according to the standard protocol of Cell Counting Kit-8 (DOJINDO LABORATORIES). Specifically, 10 µL of the reagent was added per well and the cells were cultured for 4 h. at 37° C. under a 5% $CO_2$ environment, then, the number of living cells was determined by measuring an absorbance of 450 nm by a micro plate reader (BioTek). Total 4 wells excluding the maximum and the minimum absorbance values of each group were adpoted for the analysis. Viability of the Control siRNA group and the ARHGAP26 siRNA group was determined by subtracting the absorbance of the medium group from the absorbance of each group (hereinafter referred to as the correction value), and setting the correction value of the Control siRNA group as 100%. Student's t-test was used for the significance test between Control siRNA group and ARHGAP26 siRNA group. Statistical significance was determined when the p-value was given less than 0.05.

Figure 2:
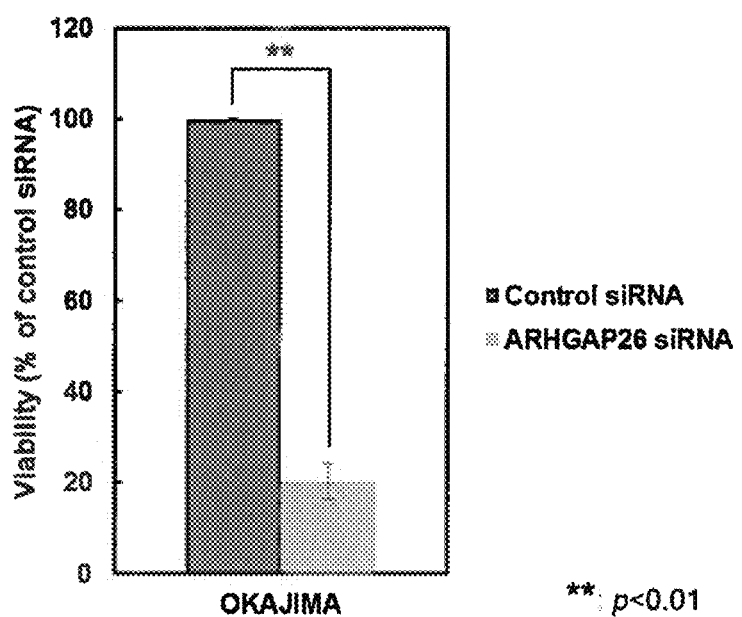
FIG. 2 shows the change in the number of viable cells in the stomach cancer cell line caused by the ARHGAP26 siRNA treatment.

Consequently, the viability of cells decreased significantly (FIG. 2) when the expression level of OCLN-ARHGAP26 fusion protein was suppressed by introducing siRNA that targets ARHGAP26 into the stomach cancer cell line OKAJIMA, which is a cell line that endogenously expresses OCLN-ARHGAP26 fusion gene. It was thus found that suppressing the expression of the fusion gene in cancer cells that endogenously express the OCLN-ARHGAP26 fusion gene inhibited the growth of cancer cells and/or decreased the survival of those cells.

Thus, it was found that the OCLN-ARHGAP26 defined the tumor advancing capacity of cancer cells.

Example 3 Detection of OCLN-ARHGAP26 Fusion Gene

Total RNA prepared from the stomach cancer cell lines KATO-III (JCRB0611, JCRB cell bank) and HSC-39 (provided from National Cancer Center Japan, Animal Experiment Section) and stomach cancer cell lines NSC-9C, NSC-6C and NSC-16C that were established at the National Cancer Center Japan, Biomarker Search Section, in addition to the stomach cancer cell line OKAJIMA that expresses an OCLN-ARHGAP26 fusion gene shown in Example 1, were reverse-transcribed into cDNA using reverse transcriptase (SuperScriptIII; Life Technologies) and oligo(dT) primer (oligo(dT)20 primer; Life Technologies).

Figure 3:
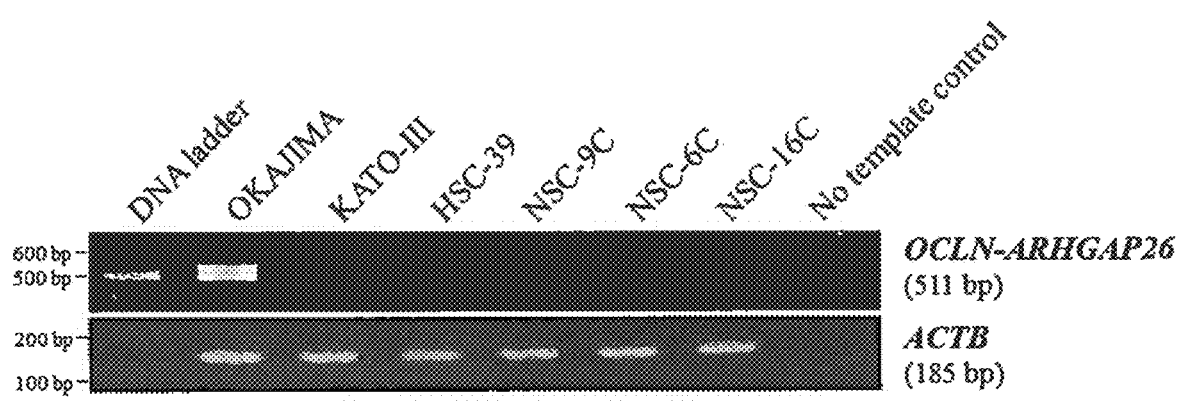
FIG. 3 shows a result of amplification by PCR of a region containing a fusion point of an OCLN-ARHGAP26 fusion gene.

Next, primers of OCLN-ARHGAP26_O5A12_partial fwd02 represented by SEQ ID NO: 7 and OCLN-ARHGAP26_O5A12_partial rev02 of SEQ ID NO: 8 were used to perform PCR (2 min. at 94° C., followed by 15 sec. at 94° C., 15 sec. at 55° C., and 1 min. at 68° C., 30 cycles) using DNA polymerase (AccuPrime Taq DNA Polymerase; Life Technologies) and cDNA obtained above as a template (200 ng when converted to total RNA). Likewise, to confirm the equal amount of cDNA template in the reactions, primers of ACTB_F2 represented by SEQ ID NO: 9 and ACTB_R2 represented by SEQ ID NO: 10 were used to perform PCR (2 min. at 94° C., followed by 15 sec. at 94° C., 15 sec. at 55° C., and 1 min. at 68° C., 25 cycles) using the same DNA polymerase as above. Electrophoresis was performed with 2% agarose gel (Lonza) after PCR reaction, and about 500 bp PCR product was amplified only at the stomach cancer cell line OKAJIMA which was already confirmed the expression of OCLN-ARHGAP26 fusion gene (FIG. 3). The PCR product amplified by the aforementioned primer set was 511 bp according to the nucleotide sequence of the fusion gene identified in Example 1. Therefore, it was shown that it is possible to detect the fusion gene expressed in cancer cells with PCR method.

Example 4 Evaluation of the Viability of Stomach Cancer Cell Line Expressing OCLN-ARHGAP26 Fusion Gene Under Suppression of OCLN-ARHGAP26 Fusion Protein Expression The stomach cancer cell line OKAJIMA that expresses OCLN-ARHGAP26 fusion gene shown in Example 1 was cultured in RPMI-1640 medium containing 10% bovine serum, then the target siRNA was introduced according to the standard protocol of a transfection reagent Dharma-FECT1 (T2001-03, GE Healthcare). Specifically, the aforementioned cancer cells were seeded at $2 \times 10$ cells per well in a 12 well plate (3815-012, AGC TECHNO GLASS Co., Ltd.), then two siRNAs targeting OCLN (Ambion s9814 and s458015 (both by Life Technologies)) and three siRNAs targeting ARHGAP26 (Ambion s23013, s23015 (both by Life Technologies) and SI03077690 (Qiagen)) were added to the cells at 75 pmol each (final concentration 75 nM), and cultured for 72 h. at 37° C. under a 5% $CO_2$ environment. At the same time, AllStars Negative Control siRNA (1027280, Qiagen) was similarly added to the cells as a negative control and siRNA (SI02653770, Qiagen) that targets KIF11 was similarly added to the cells as a positive control of apoptosis, and the cells were cultured for 72 h. at 37° C. under a 5% $CO_2$ environment. Among the siRNAs targeting ARHGAP26, s23015 was expected to target only wild-type ARHGAP26 and not OCLN-ARHGAP26 based on its sequence.

The suppressive activity of siRNA to the OCLN-ARHGAP26 fusion protein expression was evaluated by Western blot. Specifically, the cultured cells were dissolved in the Cell Lysis Buffer (9803, Cell Signaling Technology, Japan) of a 1× concentration comprising a protease inhibitor cocktail (25955-11, Nacalai) and a Halt Protease and Phosphatase Inhibitor Cocktail (78441, Thermo Fisher Scientific) each at a 1/100 amount to extract protein. The protein concentration was measured by BCA Protein Assay Kit (23227, Thermo Fisher Scientific). The protein extract was loaded onto a NuPAGE Novex 4-12% Bis-Tris Gel (NP0322BOX, Thermo Fisher Scientific) so that there will be 4 μg of target protein extract per lane, and gel electrophoresis was performed for 40 min. under a condition of 180 V, followed by transferred to a PVDF membrane (162-0176, Bio-Rad) under a condition of 120 min., 190 mA using a twin mini buffer transfer device (BE-351W, Biocraft). Then, the membrane was blocked with PVDF Blocking Reagent for Can Get Signal (NYPBR01, TOYOBO) for 1 h. at room temperature. The membrane was shaken in a primary antibody solution of anti-ARHGAP26 antibody (HPA035107, Atlas Antibodies) and anti-β-Actin antibody (4967S, Cell Signaling Technology) respectively diluted with Can Get Signal Immunoreaction Enhancer Solution1 (NKB-201, TOYOBO) to a rate of 1:1,000, and reacted overnight at 4° C. After washing with Tris buffer solution containing 0.2% Tween 20 (hereinafter referred to as a washing buffer), the membrane was shaken in a secondary antibody solution of HRP labeled anti-rabbit antibody (NA9340, GE Healthcare) diluted with Can Get Signal Immunoreaction Enhancer Solution2 (NKB-301, TOYOBO) to a rate of 1:10,000, and reacted for 1 h. at room temperature. After washing with a washing buffer, the ECL Prime Western Blotting Detection Reagent (RPN2232, GE Healthcare) was added onto the membrane and the chemiluminescence signal was detected from the membrane using LAS-4010 (GE Healthcare). As a result of Western bloting experiment, it was confirmed that the expression of OCLN-ARHGAP26 fusion protein was suppressed by two OCLN siRNAs and two ARHGAP26 siRNAs, other than s23015.

To evaluate the impact of OCLN-ARHGAP26 fusion gene on the viability of the cancer cells, transfection of siRNAs targeting OCLN, ARHGAP26 and the control siRNA to the stomach cancer cell line OKAJIMA was performed under the same condition as mentioned above. After 24 h., the medium was changed to RPMI-1640 medium containing 10% bovine serum, and the cells were seeded at $1 \times 10^3$ cells per well to a 96 well plate (3860-096, AGC TECHNO GLASS Co., Ltd.), at 100 μL each, so that each group was seeded in 3 wells, and wells added only RPMI-1640 medium containing 10% bovine serum without any cells seeded thereto (hereinafter referred to as the medium group), and the cells were subjected to further culturing at 37° C. under an environment of 5% $CO_2$ for 48 h. (hereinafter referred to as day 3) and 120 h. (hereinafter referred to as day 6). Further, as a control for normalization, plates in which cells are only seeded and not cultured were prepared (herein after day 1). The number of living cells was determined according to the standard protocol of Cell Titer Glo Luminescent Cell Viability Assay (G7571, Promega Corp.) at the time point given above. Specifically, 100 μL of a reagent was added per well and the cells were incubated for 10 min. at room temperature, then, the number of living cells was determined by measuring the luminescence by a micro plate reader Infinite M1000 (Deccan). The viability of the siRNA treated cell group of each time point was obtained by subtracting the luminescence of the medium group from the luminescence of each group (hereinafter referred to as the correction value), and setting the correction value of the siRNA treated group on day 1 as 100%.

Figure 4:
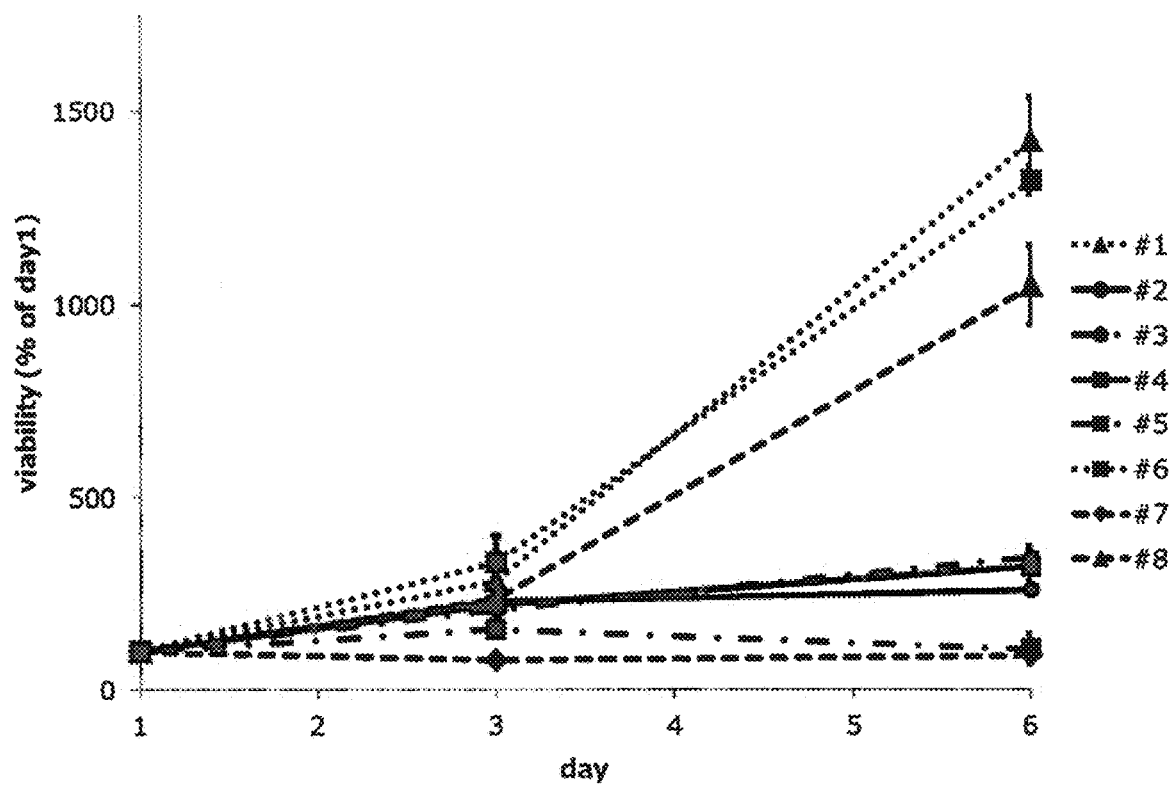
FIG. 4 shows a change caused by an OCLN siRNA treatment, and an ARHGAP26 siRNA treatment in the number of viable cells in the stomach cancer cell line over time.

Consequently, the viability of cells decreased significantly (FIG. 4) by the transfection of siRNA targeting a fusion gene to suppress the expression of the OCLN-ARHGAP26 fusion protein in the stomach cancer cell line OKAJIMA, which is a cell line that endogenously expresses OCLN-ARHGAP26 fusion gene (FIG. 4). It was thus found that suppressing the expression of the fusion gene in cancer cells that endogenously express the OCLN-ARHGAP26 fusion gene inhibited the growth of cancer cells and/or decreased the survival of those cells.

Therefore, it was shown that OCLN-ARHGAP26 is involved in the cancer cell's ability to expand tumor.

INDUSTRIAL APPLICABILITY

The detection method of the present invention is a method for detecting a fusion gene composed of the OCLN gene and the ARHGAP26 gene, and it is useful as a method for detecting and diagnosing cancer in a subject. Further, the primer set and the detection kit of the present invention may be used in a method of the present invention.

The invention claimed is:

1. A method for amplifying a fusion gene composed of part of an occludin (OCLN) gene and part of a Rho GTPase activating protein 26 (ARHGAP26) gene in a sample, wherein the method comprises amplifying a nucleic acid present in the sample with a primer pair consisting of a sense primer consisting of at least 16 consecutive bases between base number 1 to 891 of SEQ ID NO: 1 and an antisense primer consisting of an oligonucleotide complementary to an oligonucleotide of at least 16 consecutive bases between base number 892 to 2064 of SEQ ID NO: 1.

2. The method according to claim 1, wherein the method amplifies portion of a nucleic acid encoding a polypeptide comprising SEQ ID NO: 2, including the fusion portion of the fusion gene.

3. The method according to claim 1, wherein the sample is from a human subject, and the subject is a cancer patient.

4. The method according to claim 3, wherein the subject has stomach cancer.

5. The method according to claim 1, wherein the method amplifies a portion of SEQ ID NO: 1, including the fusion portion of the fusion gene.

* * * * *